United States Patent [19]

Maurer et al.

[11] 4,323,571
[45] Apr. 6, 1982

[54] COMBATING PESTS WITH 2-SUBSTITUTED-ALKYL-5-SUBSTITUTED-N,N-DIMETHYLCARBAMIC ACID O-PYRIMIDIN-6-YL ESTERS

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 161,540

[22] Filed: Jun. 20, 1980

[30] Foreign Application Priority Data

Jul. 12, 1979 [DE] Fed. Rep. of Germany ....... 2928185

[51] Int. Cl.$^3$ .................................. C07D 239/24
[52] U.S. Cl. ............................ 424/251; 544/319
[58] Field of Search .............. 544/309, 319, 335; 424/251

[56] References Cited

U.S. PATENT DOCUMENTS 4,200,637 4/1980 Maurer et al. .................. 544/319
4,215,122 7/1980 Drabek .......................... 424/251
4,234,587 11/1980 Maurer et al. .................. 544/319

FOREIGN PATENT DOCUMENTS 22000 11/1972 European Pat. Off.
1443910 5/1966 France.
0281966 8/1949 Switzerland.

*Primary Examiner*—Nicholas S. Rizzo
*Attorney, Agent, or Firm*—Sprung, Felfe, Horn, Lynch & Kramer

[57] ABSTRACT

2-Substituted-alkyl-5-substituted-N,N-dimethyl-carbamic acid O-pyrimidin-6-yl esters of the formula

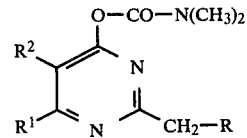

in which
R and $R^2$ each independently is alkoxy, alkylthio, alkylsulphinyl or alkylsulphonyl and
$R^1$ is hydrogen or alkyl, which possess pesticidal properties. The hydroxypyrimidines corresponding to the esters are also new.

10 Claims, No Drawings

COMBATING PESTS WITH 2-SUBSTITUTED-ALKYL-5-SUBSTITUTED-N,N-DIMETHYLCARBAMIC ACID O-PYRIMIDIN-6-YL ESTERS

The invention relates to certain new N,N-dimethyl-carbamic acid O-pyrimidinyl esters, to a process for their preparation and to their use as agents for combating pests, especially as insecticides.

It is known that certain N,N-dialkyl-carbamic acid O-pyrimidinyl esters, for example N,N-dimethylcarbamic acid O-(2-isopropyl-6-methyl-pyrimidin-4-yl) ester and O-(2-methylthio-6-methyl-pyrimidin-4-yl) ester, have insecticidal properties (see French Patent Specification No. 1,443,910 and U.S. Pat. No. 2,694,712).

However, the insecticidal action of these compounds is not always satisfactory, especially in the case of low concentrations of active compound and when small amounts are applied.

The present invention now provides (1), as new compounds, the N,N-dimethylcarbamic acid O-pyrimidinyl esters of the general formula

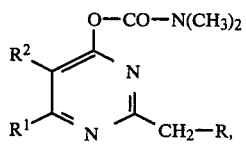   (I)

in which
R and $R^2$ are identical or different and individually represent alkoxy, alkylthio, alkylsulphinyl or alkylsulphonyl and
$R^1$ represents hydrogen or alkyl.

Preferred compounds of the formula (I) are those in which
R and $R^2$ are identical or different and individually represent alkoxy, alkylthio, alkylsulphinyl or alkylsulphonyl, in each case with 1 to 6 (especially with 1 to 3) carbon atoms, and
$R^1$ represents hydrogen or alkyl with 1 to 6 (especially with 1 to 4) carbon atoms.

Surprisingly, the N,N-dimethyl-carbamic acid O-pyrimidinyl esters according to the invention exhibit a considerably more powerful insecticidal action than the compounds of analogous structure and the same type of action which are known from the state of the art.

The invention also provides (2) a process for the preparation of an N,N-dimethyl-carbamic acid O-pyrimidinyl ester of the formula (I), characterized in that (a) a hydroxy-pyrimidine of the general formula

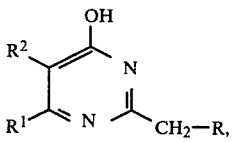   (II)

in which
R, $R^2$ and $R^1$ have the meanings indicated above, is reacted with an N,N-dimethyl-carbamic acid halide of the general formula $$Hal-CO-N(CH_3)_2 \quad (III),$$

in which
Hal represents chlorine or bromine, if appropriate in the presence of an acid acceptor and if appropriate using a diluent, or (b) a hydroxy-pyrimidine of the formula (II) above, in which
R, $R^2$ and $R^1$ have the meanings indicated above, is reacted with phosgene and then with dimethylamine, if appropriate in the presence of an acid acceptor and if appropriate using a diluent, or (c) an N,N-dimethyl-carbamic acid O-pyrimidinyl ester of the formula (I),
in which at least one of R and $R^2$ represents alkylthio, is reacted with an equimolar amount of hydrogen peroxide,
if appropriate using a diluent, or (d) an N,N-dimethyl-carbamic acid O-pyrimidinyl ester of the formula (I),
in which at least one of R and $R^2$ represents alkylthio, is reacted with at least two molar equivalents of m-chloroperbenzoic acid, if appropriate in the presence of a diluent.

It will be understood that process variant (c) is limited to the preparation of compounds (I) in which R and/or $R^2$ represent alkylsulphinyl and that process variant (d) is limited to the preparation of compounds (I) in which R and/or $R^2$ represent alkylsulphonyl.

The invention also provides (3) the new hydroxypyrimidines of the general formula

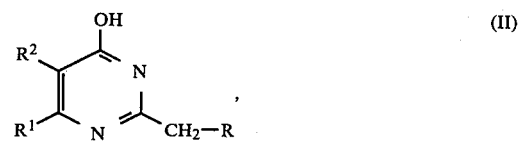   (II)

in which
R, $R^1$ and $R^2$ have the meanings indicated under (1), and (4) a process for the preparation of a hydroxypyrimidine of the formula (II), characterized in that (a) an α-substituted acetic acid ester of the general formula $$R^2-CH_2-COOR^3 \quad (IV),$$

in which
$R^2$ has the meaning indicated above and
$R^3$ represents alkyl with 1-4 carbon atoms, is reacted with an ester of the general formula $$R^1-COOR^4 \quad (V),$$

in which
$R^1$ has the meaning indicated under (1) and
$R^4$ represents alkyl with 1-4 carbon atoms, and with an α-substituted acetamidine of the general formula

   (VI)

in which

R has the meaning indicated under (1), or (b) a 5-substituted 2-chloromethyl-6-hydroxypyrimidine of the general formula

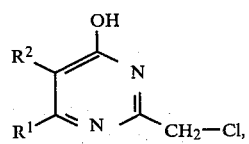

(VII)

in which
R$^2$ and R$^1$ have the meanings indicated under (1), is reacted with an alkali metal alcoholate or mercaptide of the general formula R'—X-alkali metal  (VIII), in which
R' represents $C_{1-4}$ alkyl,
X represents O or S and
alkali metal represents an alkali metal ion.

If, for example, N,N-dimethyl-carbamic acid chloride is used as a starting substance in process variant (a), phosgene and dimethylamine are used as starting substances in process variant (b), 2-ethoxy-methyl-4-isopropyl-5-methylthio-6-hydroxy-pyrimidine being used as a further starting substance in both process variants, N,N-dimethylcarbamic acid O-(2-methylthiomethyl-4-tert.-butyl-5-isopropoxy-pyrimidin-6-yl) ester and hydrogen peroxide are used as starting substances in process variant (c) and N,N-dimethyl-carbamic acid O-(2-methoxymethyl-5-methylthiopyrimidin-6-yl) ester and m-chloroperbenzoic acid are used as starting substances in process variant (d), the corresponding reactions can be outlined by the following equations:

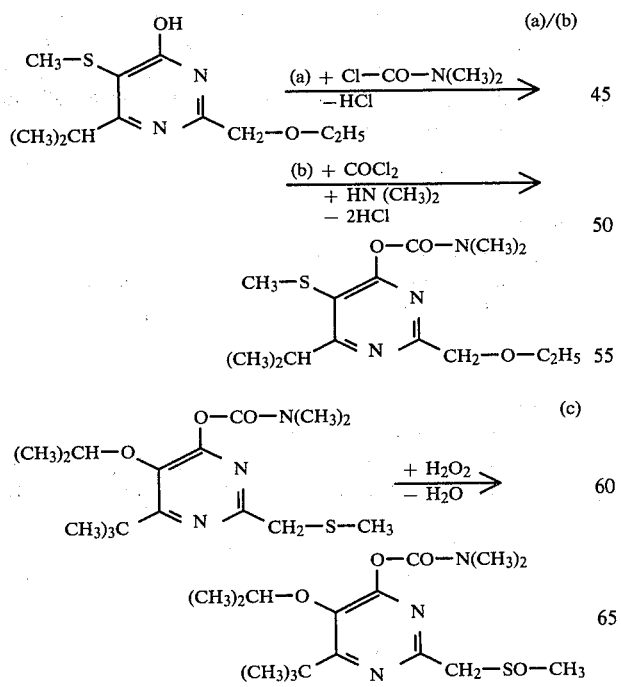

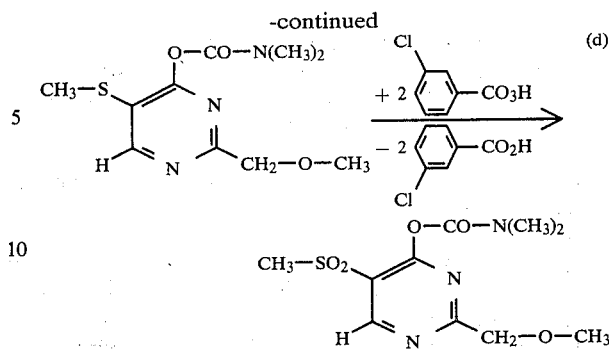

Formula (II) provides a definition of the hydroxypyrimidines to be used as starting substances in process variants (a) and (b). Preferably, in that formula, R, R$^2$ and R$^1$ have those meanings which have already been mentioned as preferred in the case of the definition of R, R$^2$ and R$^1$ in formula (I).

Examples of the compounds of the formula (II) which may be mentioned are: 2-methylthiomethyl-5-methoxy-, 2-methoxymethyl-5-methoxy-, 2-ethylthiomethyl-5-methoxy-, 2-n-propylthiomethyl-5-methoxy-, 2-methylthiomethyl-5-ethoxy, 2-methylthiomethyl-5-methylthio-, 2-methylthiomethyl-5-iso-propoxy-, 2-methylthiomethyl-5-ethoxy-, 2-methylthiomethyl-4-methyl-5-methylthio-, 2-methylthiomethyl-4-ethyl-5-methylthio-, 2-methylthiomethyl-4-tert.-butyl-5-methylthio-, 2-iso-propylthiomethyl-5-methoxy-, 2-methylthiomethyl-5-n-propoxy-, 2-ethylthiomethyl-5-ethoxy-, 2-methylthiomethyl-5-ethylthio- and 2-ethylthiomethyl-5-ethoxy-6-hydroxy-pyrimidine.

The hydroxy-pyrimidines of the formula (II) have not hitherto been described in the literature. These compounds are obtained:

(a) by reacting alkoxy- or alkylthio-acetic acid esters, for example methoxyacetic acid methyl ester, with such esters as, for example, formic acid methyl ester, in the presence of a base, for example sodium methylate, and if appropriate using a diluent, for example methanol, at a temperature between 0° and 50° C., and reacting the products thereby obtained with alkoxy- or alkylthio-acetamidines or hydrochlorides thereof, for example methylthio-acetamidine hydrochloride, also at a temperature between 0° and 50° C. For working up, the solvent is stripped off in vacuo, the residue is dissolved in water and the pH value is adjusted to about 6. The solution is extracted with a water-immiscible solvent, for example methylene chloride, and the solvent is distilled off from the extract, whereupon the product is obtained as a solid or oily residue. Alkylthiomethyl-hydroxy-pyrimidines of the formula (II) can be oxidized with oxidizing agents, for example hydrogen peroxide or m-chloro-perbenzoic acid, at temperatures between 0° and 50° C., if appropriate using a diluent, for example acetic acid or chloroform, to give the corresponding alkylsulphinylmethyl- or alkylsulphonylmethylhydroxypyrimidines.

Hydroxy-pyrimidines of the formula (II) are also obtained (b) by reacting 5-alkoxy- or 5-alkylthio-2-chloromethyl-6-hydroxy-pyrimidines with alkali metal alcoholates or mercaptides at temperatures between 20° and 100° C., if appropriate using a diluent, for example methanol or acetonitrile. For working up, the pH value is adjusted to about 6 and the solvent is distilled off. The residue is digested with ethanol, the suspension is filtered and the filtrate is freed from solvent by vacuum distillation. The products are thereby obtained in a solid or oily form.

The 5-alkoxy- or 5-alkylthio-2-chloromethyl-6-hydroxy-pyrimidines to be employed as precursors are obtained by reacting chloroacetonitrile with ammonium chloride in the presence of a base, for example sodium methylate, if appropriate using a diluent, for example methanol, at a temperature between $-10°$ and $+30°$ C. and then reacting the products obtained by reacting alkoxy- or alkylthio-acetic acid esters with formic acid esters in the presence of a base, for example sodium methylate, with the products thereby obtained, likewise at temperatures between $-10°$ and $+30°$ C. and if appropriate in the presence of a base, for example sodium methylate, if appropriate using a diluent, for example methanol. For working up, the pH value is adjusted to about 5, the mixture is diluted with water and, if appropriate, the organic solvent is distilled off. The product crystallizes out of the aqueous solution.

N,N-Dimethyl-carbamic acid chloride may be mentioned as an example of the carbamic acid halides of the formula (III) to be used in process variant (a). This compound has been known for a long time, as have the reaction components phosgene and dimethylamine to be employed in process variant (b).

The formula (I) provides a definition of the N,N-dimethyl-carbamic acid O-pyrimidin-yl esters to be used as starting compounds in process variants (c) and (d), with the proviso that at least one of the radicals R and $R^2$ represents alkylthio.

Preferably, in this formula, R, $R^2$ and $R^1$ have those meanings which have already been mentioned as preferred in the definition of R, $R^2$ and $R^1$ in formula (I).

Examples which may be mentioned of the compounds of the formula (I) which can be used as starting compounds are: N,N-dimethylcarbamic acid O-(2-methylthiomethyl-5-methoxy-pyrimidin-6-yl) ester, O-(2-methylthiomethyl-5-ethoxy-pyrimidin-6-yl) ester, O-(2-ethylthiomethyl-5-methoxy-pyrimidin-6-yl) ester, O-(2-n-propylthiomethyl-5-methoxy-pyrimidin-6-yl) ester, O-(2-methylthiomethyl-5-iso-propoxy-pyrimidin-6-yl) ester, O-(2-methylthiomethyl-5-methylthio-pyrimidin-6-yl) ester, O-(2-methylthiomethyl-5-ethylthio-pyrimidin-6-yl) ester, O-(2-methylthiomethyl-4-methyl-5-methylthio-pyrimidin-6-yl) ester, O-(2-methylthiomethyl-4-ethyl-5-methylthio-pyrimidin-6-yl) ester, O-(2-methylthiomethyl-4-tert.-butyl-5-methylthio-pyrimidin-6-yl) ester, O-(2-isopropylthiomethyl-5-methoxy-pyrimidin-6-yl) ester, O-(2-methylthiomethyl-5-n-propoxy-pyrimidin-6-yl) ester, O-(2-methylthiomethyl-5-iso-propoxy-pyrimidin-6-yl) ester and O-(2-ethylthiomethyl-5-ethoxy-pyrimidin-6-yl) ester.

The oxidizing agents hydrogen peroxide and m-chloroperbenzoic acid to be used in process variants (c) and (d) are known compounds.

In general, process variants (a) to (d) for the preparation of the new N,N-dimethyl-carbamic acid O-pyrimidinyl esters are carried out using a diluent. Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Process variant (c) is advantageously carried out using an aliphatic carboxylic acid, for example formic acid, acetic acid or propionic acid, as the diluent.

Process variants (a) and (b) are in general carried out using an acid acceptor. Any of the customary acid-binding agents can be used as the acid acceptor. Acid-binding agents which have proved particularly suitable are alkali metal carbonates and alcoholates, such as sodium carbonate, potassium carbonate, sodium methylate or ethylate or potassium methylate or ethylate, and furthermore aliphatic, aromatic or heterocyclic amines, for example triethylamine, trimethylamine, dimethylaniline, dimethylbenzylamine or pyridine.

The process variants according to the invention are in general carried out at a temperature between 0° and 150° C. The temperature range between 20° and 100° C. is preferred for process variant (a) and the range between 0° and 50° C. is preferred for process variants (b), (c) and (d). The reactions are in general carried out under normal pressure.

For carrying out process variants (a) and (b), between 1.0 and 1.3, preferably between 1.0 and 1.15, mols of N,N-dimethylcarbamic acid halide or phosgene and dimethylamine are employed per mol of hydroxypyrimidine of the formula (II). The reaction is in general carried out in a diluent, in the presence of an acid acceptor. When the reaction has ended, the mixture is filtered and the solvent is distilled off from the filtrate in vacuo.

In process variant (c), the reaction components are employed in equimolar amounts. If water-miscible diluents are used, these are distilled off in vacuo when the reaction has ended. The residue is then dissolved in a water-immiscible solvent, for example methylene chloride, and working up is carried out by customary methods, for example by washing, drying and filtering the solution and distilling off the solvent from the filtrate.

In process variant (d), the m-chloro-perbenzoic acid used as the oxidizing agent is usually employed in excess, and in particular between 2 and 3 mols are preferably employed per mol of N,N-dimethyl-carbamic acid O-(alkylthiomethyl-pyrimidinyl) ester. The reaction is in general carried out in a water-immiscible solvent. When the reaction has ended, the mixture is washed until neutral, dried and filtered and the solvent is distilled off from the filtrate in vacuo.

The new compounds are obtained in the form of oils, some of which cannot be distilled without decomposition, but which are freed from the last volatile constituents by so-called "incipient distillation," that is to say by prolonged heating to moderately elevated temperatures under reduced pressure, and are purified in this manner. They are characterized by their refractive index.

If, after distilling off the solvent, the new compounds are obtained in a solid form, they are purified by recrystallization. In this case, they are characterized by their melting point.

The N,N-dimethyl-carbamic acid O-pyrimidinyl esters according to the invention are distinguished by a high insecticidal activity, and in particular also by a root systemic activity. They can thus be used for protecting useful plants against insects, in agriculture and forestry, and in he field of hygiene and in the protection of stored products.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigeralla immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haemtopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllochistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannnia spp., *Bibio hortulanus, Oscinella frit,* Phrobia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispsersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl-sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyalcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (especially arthropods and in particular insects) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The novel compounds could be prepared as follows:

EXAMPLE 1

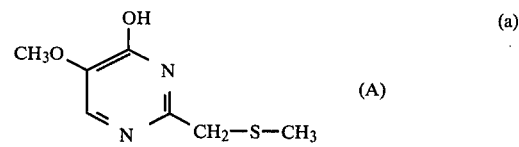

(a)

(A)

5.4 g (0.1 mol) of solid sodium methylate were added in portions to a mixture of 10.4 g (0.1 mol) of methoxyacetic acid methyl ester and 6 g (0.1 mol) of formic acid methyl ester at 20°-25° C. and the mixture was subsequently stirred at room temperature for 5 hours. A further 5.4 g (0.1 mol) of sodium methylate, dissolved in 40 ml of methanol, were then added, 14.1 g (0.1 mol) of methylthioacetamidine hydrochloride were subsequently added to the mixture and the mixture was then stirred at room temperature for 24 hours. The solvent was now stripped off in vacuo, the residue was dissolved in 300 ml of water and the solution was brought to pH 6 by adding concentrated hydrochloric acid. The solution was then twice extracted by shaking with 150 ml of methylene chloride each time, the organic phase was dried over sodium sulphate and the solvent was distilled off in vacuo. 13 g (70% of theory) of 2-methylthiomethyl-6-hydroxy-5-methoxypyrimidine were obtained in this manner in the form of a light brown powder with a melting point of 102° C.

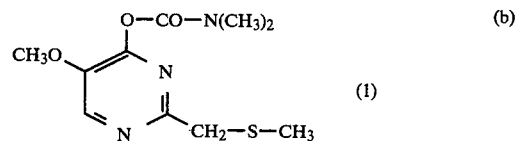

(b)

(1)

A mixture of 18.6 g (0.1 mol) of 2-methylthiomethyl-6-hydroxy-5-methoxypyrimidine, 16.6 g (0.12 mol) of potassium carbonate, 200 ml of acetonitrile and 10.8 g (0.1 mol) of dimethylcarbamic acid chloride was boiled under reflux for 7 hours, cooled to room temperature and then filtered. The filtrate was evaporated in vacuo. 19.5 g (76% of theory) of N,N-dimethyl-carbamic acid O-(2-methylthiomethyl-5-methoxypyrimidin-6-yl) ester remained in the form of beige crystals with a melting point of 97° C.

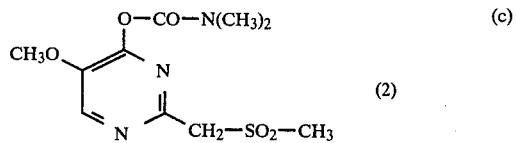

(c)

(2)

11.2 g of a 30 percent strength solution of $H_2O_2$ in water were added dropwise to a solution of 25.7 g (0.1 mol) of N,N-dimethyl-carbamic acid O-(2-methyl-thiomethyl-5-methoxy-pyrimidin-6-yl) ester in 100 ml of glacial acetic acid at 5°-10° C. The mixture was then subsequently stirred at room temperature for 18 hours, the solvent was distilled off in vacuo and the residue was dissolved in 100 ml of methylene chloride. The solution was washed once with 40 ml of 50 percent strength potassium carbonate solution, dried over sodium sulphate and evaporated in vacuo. 22.4 g (82% of theory) of N,N-dimethyl-carbamic acid O-(2-methylsulphinylmethyl-5-methoxy-pyrimidin-6-yl) ester were obtained in this manner in the form of yellow crystals with a melting point of 112° C.

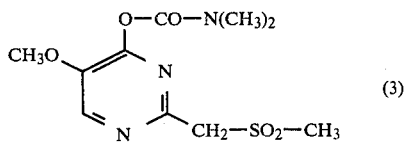

(d)

(3)

A solution of 44.5 g (0.22 mol) of m-chloro-perbenzoic acid in 500 ml of chloroform was added to a solution of 25.7 g (0.1 mol) of N,N-dimethyl-carbamic acid O-(2-methylthiomethyl-5-methoxypyrimidin-6-yl) ester in 100 ml of chloroform at 0°–5° C. and the mixture was then subsequently stirred at room temperature for 18 hours. The insoluble material was then filtered off and the filtrate was shaken with 50 ml of 50 percent strength potassium carbonate solution. After drying the product phase over sodium sulphate, the solvent was distilled off in vacuo. 28.3 g (95% of theory) of N,N-dimethyl-carbamic acid O-(2-methylsulphonylmethyl-5-methoxypyrimidin-6-yl) ester remained in the form of colorless crystals with a melting point of 122° C.

EXAMPLE 2

(a) The 2-chloromethyl-6-hydroxy-5-methoxypyrimidine (B) to be used as the starting material could be prepared, for example, as follows:

151.2 g (2 mols) of chloroacetonitrile were added to a solution of 10.8 g (0.2 mol) of sodium methylate in 500 ml of methanol at 0°–5° C., 117.6 g (2.2 mols) of ammonium chloride were then added at 15°–20° C. and the mixture was subsequently stirred at room temperature for 4 hours. Thereafter, it was added, at 0°–5° C., to a mixture of 208 g (2 mols) of methoxyacetic acid methyl ester, 120 g (2 mols) of formic acid methyl ester and 108 g (2 mols) of solid sodium methylate, which had first been stirred at room temperature for 5 hours. A solution of 108 g (2 mols) of sodium methylate in 400 ml of methanol was then added at 0°–5° C. and the reaction mixture was subsequently stirred at 0°–5° C. for 24 hours. The pH value was adjusted to 5 by adding concentrated hydrochloric acid, while still cooling, and water was then added in an amount such that a clear solution was formed. The methanol was distilled out of the reaction mixture in vacuo, the aqueous solution which remained was cooled, and the product which had precipitated was then filtered off. 140 g (40% of theory) of 2-chloromethyl-6-hydroxy-5-methoxypyrimidine were obtained in this manner in the form of a sand-colored powder with a melting point of 188° C. (decomposition).

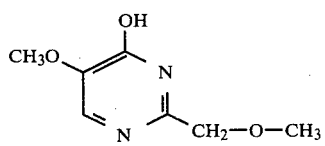

(b)

A mixture of 17.5 g (0.1 mol) of 2-chloromethyl-6-hydroxy-5-methoxypyrimidine, 11.7 g (0.22 mol) of sodium methylate and 150 ml of methanol was boiled under reflux for 8 hours. The cooled mixture was then brought to pH 5–6 by adding hydrochloric acid, the solvent was distilled off in vacuo and the residue was triturated with 50 ml of ethanol. The suspension thus obtained was filtered and the filtrate was evaporated in vacuo. 12.1 g (71% of theory) of 2-methoxymethyl-6-hydroxy-5-methoxy-pyrimidine with a melting point of 87° C. remained.

The following intermediates of the general formula

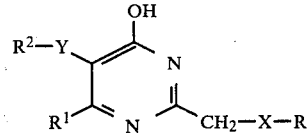

could be prepared analogously to one of Examples 1a and 2a/b:

TABLE 1

| Example No. | R | $R^1$ | $R^2$ | X | Y | Yield (% of theory) | Melting point (°C.) |
|---|---|---|---|---|---|---|---|
| C | $C_2H_5$ | H | $CH_3$ | S | O | 76 | 151 |
| D | $C_3H_7$ | H | $CH_3$ | S | O | 28 | 119 |
| E | $CH_3$ | H | $C_2H_5$ | S | O | 25 | 177 (decomposition)* |
| F | $CH_3$ | H | $CH_3$ | S | S | | |
| G | $CH_3$ | H | $i$-$C_3H_7$ | S | O | | |
| H | $CH_3$ | H | $C_2H_5$ | S | S | | |
| I | $CH_3$ | $CH_3$ | $CH_3$ | S | S | | |
| J | $CH_3$ | $C_2H_5$ | $CH_3$ | S | S | | |
| K | $CH_3$ | t.-$C_4H_9$ | $CH_3$ | S | S | | |
| L | $i$-$C_3H_7$ | H | $CH_3$ | S | O | | |
| M | $CH_3$ | H | $C_3H_7$ | S | O | | |
| N | $C_2H_5$ | H | $C_2H_5$ | S | O | | |

*HCl-Salt

The following compounds of the general formula

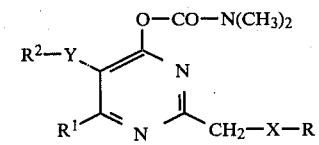

could be prepared in a manner analogous to Examples 1b–1d:

TABLE 2

| Compound No. | R | $R^1$ | $R^2$ | X | Y | Yield (% of theory) | Refractive index or melting point (°C.) |
|---|---|---|---|---|---|---|---|
| 4 | $C_2H_5$ | H | $CH_3$ | S | O | 55 | 83 |
| 5 | $C_2H_5$ | H | $CH_3$ | SO | O | 97 | 116 |
| 6 | $C_2H_5$ | H | $CH_3$ | $SO_2$ | O | 94 | 113 |
| 7 | n-$C_3H_7$ | H | $CH_3$ | S | O | | |
| 8 | $CH_3$ | H | $C_2H_5$ | S | O | | |
| 9 | $CH_3$ | H | i-$C_3H_7$ | S | O | | |
| 10 | $CH_3$ | H | $CH_3$ | O | O | 70 | 75 |
| 11 | $CH_3$ | H | $CH_3$ | S | S | | |
| 12 | $CH_3$ | H | $C_2H_5$ | S | S | | |
| 13 | $CH_3$ | $CH_3$ | $CH_3$ | S | S | | |
| 14 | $CH_3$ | $C_2H_5$ | $CH_3$ | S | S | | |
| 15 | $CH_3$ | t-$C_4H_9$ | $CH_3$ | S | S | | |
| 16 | $CH_3$ | H | $CH_3$ | SO | SO | | |
| 17 | $CH_3$ | H | $CH_3$ | $SO_2$ | $SO_2$ | | |
| 18 | $iC_3H_7$ | H | $CH_3$ | S | O | | |
| 19 | $CH_3$ | H | n-$C_3H_7$ | S | O | | |
| 20 | $C_2H_5$ | H | $C_2H_5$ | S | O | | |

The pesticidal activity of the compounds of this invention is illustrated by the following examples wherein the compounds according to the present invention are each identified by the number (given in brackets) from the preparative examples hereinabove:

EXAMPLE 3

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (1), (2), (3), (4), (5) and (6).

EXAMPLE 4

Doralis test (systemic action)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound of the desired concentration in such a way that the preparation of the active compound penetrated into the soil without wetting the shoot. The active compound was taken up by the roots and passed to the shoot.

After the specified periods of time, the destruction in % was determined. 100% meant that all the aphids had been killed; 0% meant that none of the aphids had been killed.

In this test, for example, the following compounds showed a superior activity compared to the prior art: (2), (3), (4), (5) and (6).

EXAMPLE 5

Critical concentration test/root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the compound (1) showed a superior action compared to the prior art.

It will be appreciated that the instant specification and examples are set forth by way of illustration and not limitation, and that various modifications and changes may be made without departing from the spirit and scope of the present invention.

We claim:

1. A 2-substituted-alkyl-5-substituted-N,N-dimethyl-carbamic acid O-pyrimidin-6-yl ester of the formula

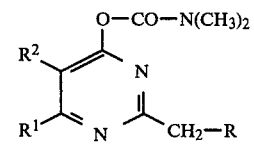

in which
R and $R^2$ each independently is alkoxy, alkylthio, alkylsulphinyl or alkylsulphonyl and
$R^1$ is hydrogen or alkyl.

2. A compound according to claim 1,
in which
R and $R^2$ each independently is alkoxy, alkylthio, alkylsulphinyl or alkylsulphonyl with 1 to 6 carbon atoms.

3. A compound according to claim 1, in which said compound is N,N-dimethy-carbamic acid O-(2-methyl-thiomethyl-5-methoxypyrimidin-6-yl) ester of the formula

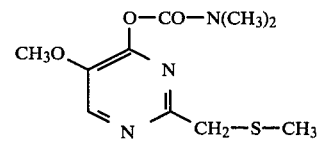

4. A compound according to claim 1, in which said compound is N,N-dimethyl-carbamic acid O-(2-methyl-sulphonylmethyl-5-methoxypyrimidin-6-yl) ester of the fomula

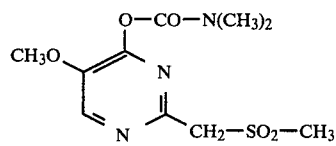

5. A compound according to claim 1, in which said compound is N,N-dimethyl-carbamic acid O-(2-ethylthiomethyl-5-methoxypyrimidin-6-yl) ester of the formula

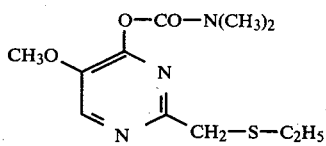

6. A compound according to claim 1, in which said compound is N,N-dimethyl-carbamic acid O-(2-ethylsulphonylmethyl-5-methoxypyrimidin-6-yl) ester of the formula

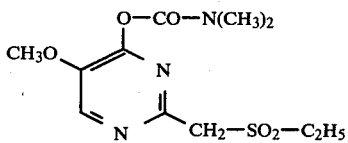

7. A compound according to claim 1, in which said compound is N,N-dimethyl-carbamic acid O-(2-methylsulphinylmethyl-5-methoxypyrimidin-6-yL) ester of the formula

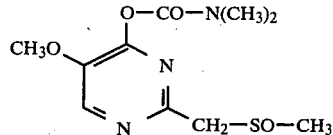

8. An insecticidal composition comprising an insecticidally effective amount of a compound according to claim 1 in admixture with a diluent.

9. A method of combating insects comprising applying to the insects, or to a habitat thereof, an insecticidally effective amount of a compound according to claim 1.

10. The method according to claim 9, in which said compound is
N,N-dimethyl-carbamic acid O-(2-methylthiomethyl-5-methoxypyrimidin-6-yl) ester,
N,N-dimethyl-carbamic acid O-(2-methylsulphonylmethyl-5-methoxypyrimidin-6-yl) ester,
N,N-dimethyl-carbamic acid O-(2-ethylthiomethyl-5-methoxypyrimidin-6-yl) ester,
N,N-dimethyl-carbamic acid O-(2-ethylsulphonylmethyl-5-methoxypyrimidin-6-yl) ester, or
N,N-dimethyl-carbamic acid O-(2-methylsulphinylmethyl-5-methoxypyrimidin-6-yl) ester.

* * * * *